(12) United States Patent
Heide

(10) Patent No.: US 10,335,533 B2
(45) Date of Patent: Jul. 2, 2019

(54) DEVICE FOR SEPARATING BLOOD INTO ITS COMPONENTS AS WELL AS A METHOD FOR DOING SO AND USE OF SUCH A DEVICE

(71) Applicant: Fresenius Medical Care Deutschland GmbH, Bad Homburg (DE)

(72) Inventor: Alexander Heide, Eppstein (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 397 days.

(21) Appl. No.: 15/034,891

(22) PCT Filed: Jan. 22, 2015

(86) PCT No.: PCT/EP2015/051201
§ 371 (c)(1),
(2) Date: May 6, 2016

(87) PCT Pub. No.: WO2015/110501
PCT Pub. Date: Jul. 30, 2015

(65) Prior Publication Data
US 2016/0279315 A1    Sep. 29, 2016

(30) Foreign Application Priority Data

Jan. 25, 2014 (DE) .................. 10 2014 000 971

(51) Int. Cl.
| | |
|---|---|
| *A61M 1/34* | (2006.01) |
| *B04B 5/04* | (2006.01) |
| *B04B 9/12* | (2006.01) |
| *A61M 1/26* | (2006.01) |
| *A61M 1/36* | (2006.01) |

(Continued)

(52) U.S. Cl.
CPC .......... *A61M 1/3496* (2013.01); *A61M 1/262* (2014.02); *A61M 1/3693* (2013.01);
(Continued)

(58) Field of Classification Search
CPC .. A61M 1/262; A61M 1/3496; A61M 1/3693; A61M 1/3696; A61M 2205/103; B04B 1/00; B04B 5/0407; B04B 5/0442; B04B 9/00; B04B 9/12; B04B 9/146; B01D 21/262
See application file for complete search history.

(56) References Cited

U.S. PATENT DOCUMENTS

| | | |
|---|---|---|
| 4,076,340 A | 2/1978 | Meinke et al. |
| 4,337,981 A | 7/1982 | Meinke |

(Continued)

FOREIGN PATENT DOCUMENTS

| | | |
|---|---|---|
| CN | 1226307 | 8/1999 |
| DE | 19801767 | 10/1999 |

(Continued)

*Primary Examiner* — Timothy C Cleveland
(74) *Attorney, Agent, or Firm* — Jacobson Holman, PLLC

(57) ABSTRACT

The invention relates to a device for separating blood into its components and a method for the same and use of such a device. The device comprises a magnetic drive device, which causes a container to rotate about its own axis, wherein the container has at least one open end and at least one inlet therein and is suspended in a magnetically floating manner.

19 Claims, 3 Drawing Sheets

Figure 1:
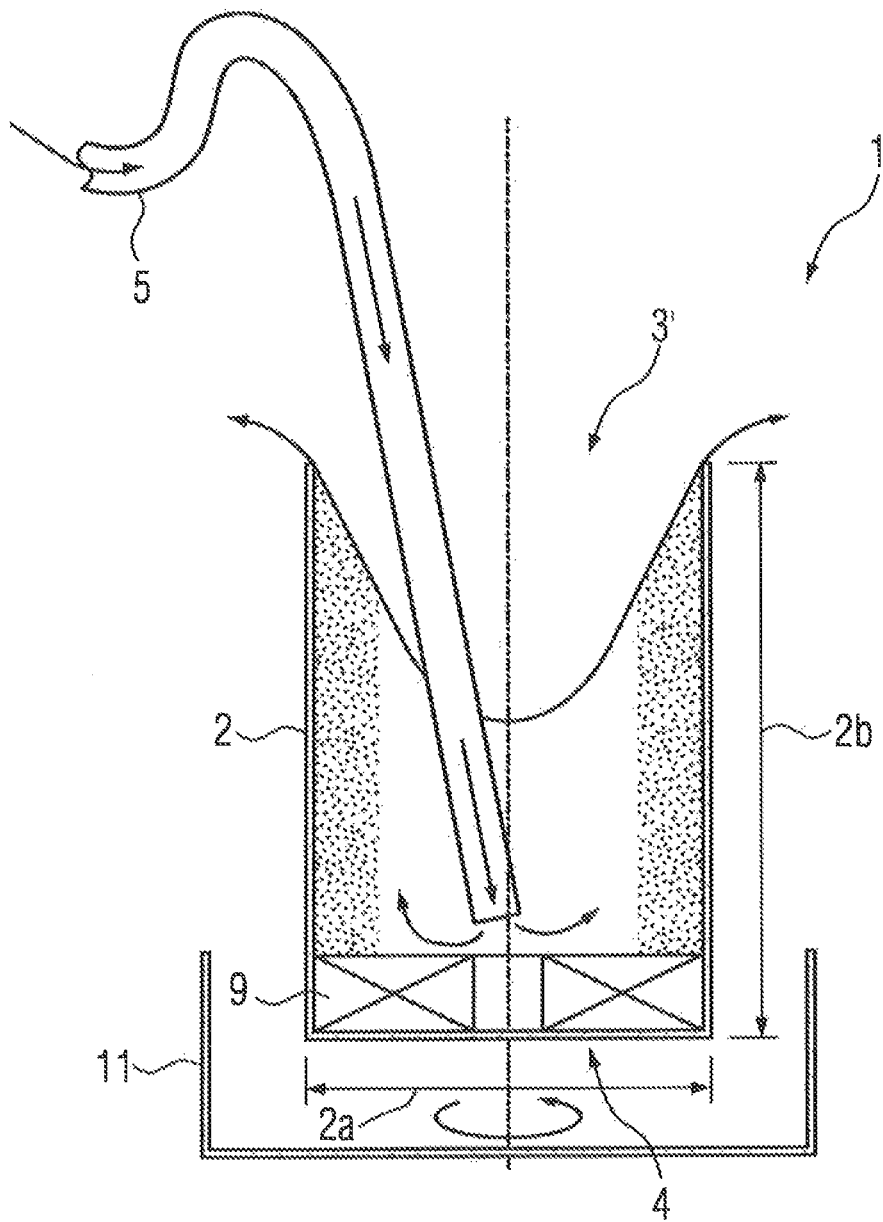

(51) Int. Cl.
  *B04B 1/00* (2006.01)
  *B04B 9/00* (2006.01)
  *B01D 21/26* (2006.01)
  *B04B 9/14* (2006.01)

(52) U.S. Cl.
  CPC ......... *A61M 1/3696* (2014.02); *B01D 21/262* (2013.01); *B04B 1/00* (2013.01); *B04B 5/0407* (2013.01); *B04B 5/0442* (2013.01); *B04B 9/00* (2013.01); *B04B 9/12* (2013.01); *B04B 9/146* (2013.01); *A61M 2205/103* (2013.01)

(56) References Cited

U.S. PATENT DOCUMENTS

| | | |
|---|---|---|
| 5,830,370 A | 11/1998 | Maloney, Jr. et al. |
| 6,100,618 A | 8/2000 | Schoeb et al. |
| 6,471,855 B1 | 10/2002 | Odak et al. |
| 6,544,162 B1 * | 4/2003 | Van Wie ............. A61M 1/3693 494/35 |
| 2002/0094281 A1 | 7/2002 | Khanwilkar et al. |

FOREIGN PATENT DOCUMENTS

| | | |
|---|---|---|
| DE | 19841835 | 3/2000 |
| DE | 10120623 | 3/2002 |
| EP | 0819330 | 1/1998 |
| EP | 0900572 | 3/1999 |
| EP | 1057534 | 12/2000 |
| EP | 1251922 | 10/2002 |
| GB | 1044264 | 9/1966 |
| GB | 1392210 | 4/1975 |
| WO | WO 97/33697 | 9/1997 |
| WO | WO 02/056992 | 7/2002 |
| WO | WO 2013/116800 | 8/2013 |

* cited by examiner

DEVICE FOR SEPARATING BLOOD INTO ITS COMPONENTS AS WELL AS A METHOD FOR DOING SO AND USE OF SUCH A DEVICE

The invention relates to the field of extracorporeal treatment of blood and the field of blood separation in particular and it concerns a device for separating blood into its components as well as a method for doing so. The invention also relates to a treatment unit having a device according to the preamble of claim 1. In addition, the invention relates to the use of a device for separating whole blood and extracting individual components from it. It is also conceivable to separate other medical and biological fluids with the help of the aforementioned device. The device may thus also be used in other fields in which the separation of fluids according to their density is desired such as in the technical, analytical and pharmaceutical fields, for example.

Human blood contains primarily three types of cells, namely erythrocytes, leukocytes and platelets, each of which has a specific function for the body. These blood cells are suspended in a complex aqueous solution of proteins and other chemicals known as plasma.

It may be desirable or necessary to separate whole blood into its components in an extracorporeal treatment of blood, for example, in order to be able to subject the individual components to a further treatment in a targeted fashion.

Blood is also separated into its components for blood transfusions when there has been a high acute or chronic blood loss, such as that associated with chronic blood diseases, for example, in the sense of a hematologic disorder necessitating restoration of a patient's blood loss.

The components of blood are administered as a concentrate for transfusion (e.g., erythrocyte concentrate, granulocyte concentrate, platelet concentrate or stem cell concentrate, immunoglobulins, human albumin or plasma and/or serum (plasma without coagulation factors)). The blood components used most often in transfusion are the erythrocytes and plasma. Plasma transfusions are often used to replenish spent coagulation factors, for example.

Separating whole blood into its components has the advantage that the patient then receives only the blood components he is lacking. Therefore, the patient does not unnecessarily come in contact with other blood components and therefore is also not exposed to the risk of an infection or adverse effect which might be associated with transfusion of other blood components. Furthermore, the individual blood component concentrates can be stored for a much longer period of time than whole blood. For example, plasma can be stored for months when frozen.

Methods for separating and collecting certain components from whole blood are mainly based on three different separation methods: bag centrifugation, membrane filtration and bell centrifugation or cell separation with the help of separation chambers.

In bag centrifugation, a bag filled with anticoagulated whole blood is centrifuged at a very high speed in a laboratory centrifuge. The blood is then exposed to many times the force of gravity. Because of the centrifugal force, the individual components of blood are separated into layers according to density. Each component of blood can then be removed individually from the bag. However, the yield and thus also the economic feasibility of bag centrifugation are limited because it is not possible to withdraw an unlimited amount of blood from a donor.

Another method, so-called hemapheresis, is of a greater burden for the donor but it offers more tolerance with respect to the amount of concentrate that can be extracted.

Hemapheresis differs from convention blood donation through the use of cell separators which have an extracorporeal circulation connected to the donor. The blood is fractionated as it is donated. This often yields preparations of only one of the components of blood, but in recent years, more efficient multicomponent methods have been developed, in which multiple components of blood can be collected in parallel.

After conclusion of this method, the unneeded blood components are returned to the donor. Larger amounts of other components can be donated in this way. Only with such a method is it possible to obtain sufficient amounts of such blood components, even those that constitute only a small percentage of the blood (e.g., platelets, stem cells), from individual donors.

So-called bell centrifugation is known as a less cost-intensive type of hemapheresis method: anticoagulated blood is placed in a container, which is in the shape of a drum, beaker, cylinder or bell.

This method is used, for example, in the cell separator from the company Haemonetics, in which the blood is separated in a so-called "Latham bell." The container is clamped in a device which rotates the container at a high speed. The centrifugal force creates an artificial gravitational field in which the cells are separated into layers according to their density. The denser cells are forced outward away from the central axis of the container and collect along the inside wall of the container. The plasma having the lowest density remains behind at the center of the container.

Separation with a bell centrifuge is less expensive because the construction is simpler and requires less material. However, blood components produced by this method have a lower purity: separated plasma may still contain residual blood cells.

The method described here is a discontinuous method, in which the withdrawal phase and/or the separation phase and the return phase are separated from one another in time. However, it is important to be sure that the extracorporeal volume does not exceed 15% of the circulating blood volume of the donor in order to prevent the circulation from collapsing. Discontinuous methods are thus slower and the amount of blood concentrate to be obtained is limited by the longest possible duration of use.

If the blood components are to be obtained in a larger volume and in a shorter period of time, so-called continuous hemapheresis is used.

In the continuous hemapheresis process, the blood components are extracted during the constant withdrawal of a small quantity of blood and simultaneous return of the blood components that are not needed. A continuous flow of blood is maintained.

Membrane filtration is known as a type of continuous hemapheresis. In this process, a membrane with a suitable pore site (e.g., 0.5 μm) is used to filter plasma out of the blood. Because of the viscous and complex properties of whole blood, however, simple filtration is not enough because the pores of the membrane are easily clogged due to cellular substances or proteins. Therefore, membrane filtration processes typically include either internal or external rotatable filter media. The rotation relative to an opposing stationary surface causes whole blood to be conveyed across a membrane surface and thus creates shearing effects, which drive the plasma through the membrane while the corpuscular components are rinsed away.

State-of-the-art membrane filtration devices can often produce a blood product with a greater purity, i.e., with regard to residual cells (e.g., leukocytes). To permit the collection of plasma, for example, from a single donor at an acceptable rate, a large membrane surface area is necessary. However, the cost of the membrane is relatively high and efficiency declines over a period of use, so membrane filtration is also practical only to a limited extent.

Mainly disposable plastic sets with an integrated separation chamber are used today for continuous processes in extracorporeal circulation. The separation chambers are closed sets of plastic, which in general have a separation channel into which the cell suspension to be separated is sent. The cell suspension is separated into individual blood components under the influence of centrifugal force. In the case of two-piece separation chambers, the separation channel is formed by a flexible film part, which is placed in a rigid receiving unit.

However, construction of the devices used here has proven to be complicated because the incoming and outgoing tubes must be prevented from twisting during rotation. Furthermore, during the preparation of concentrates using the separation chamber as described here, the separation of platelets in particular is often unclean or inadequate. Cells that have already been separated may also be entrained into a different fraction due to turbulence in the transitional area between the individual channel sections.

In addition to the target-specific density and the respective cell diameter, the centrifugal acceleration (depending on the centrifugal rotational speed and the radius of the centrifuge chamber) are important for the yield in cell separation. The higher the centrifugal acceleration, the greater is the separation rate and thus the centrifugal force and the better, i.e., the more accurately the cells are separated.

If the centrifuge container should now be as small as possible, the rate required to achieve a sufficient centrifugal force for separation must also be higher.

Acceleration of the centrifuge chamber may take place, for example, by way of a belt drive, a gearwheel drive or an electric motor.

However, all types of drives have in common the resulting disadvantages such as high running noises, high cost of maintenance, production of heat of friction and wear.

The separation rate is thus limited and accordingly the centrifuge container must have a minimum radius.

Numerous devices which work according to the aforementioned principles in separating blood into its components are already known from the prior art.

A device which operates discontinuously according to the principle of bell centrifugation is known from the document EP 1 057 534. To increase the yield and accelerate the total use time, the combination of a centrifuge bell and a membrane filter are used in this method.

EP 1 251 922 describes a disposable cassette with an integrated separation device for plasma separation, which cooperates with a reusable module.

The document DE 198 41 835 discloses a device for continuous hemapheresis, which has a separation chamber with a separation channel having a spiral curvature.

A magnetic gear for a cell separation centrifuge is known from DE 198 01 767, for example. This centrifuge has a frame on which a rack is mounted with a centrifuge chamber to rotate about the axis of the centrifuge. The transfer of force to the chamber and/or the rotating frame is a non-contact process and takes place by way of coupling elements by means of magnetic forces without any wear.

The document EP 0 819 330 discloses a rotary pump, in which the impeller wheel is mounted in a suspended mount in the interior of the pump housing due to magnetic forces and is driven by a rotational field generated by a stator disposed outside of the pump housing.

The document EP 0 900 572 describes a centrifugal pump for pumping blood in which the impeller wheel is also supported magnetically and in a non-contact mount in the pump housing and is driven by an electromagnetic rotary field.

The invention is based on the object of making available a device and a method which make it possible to separate blood into its components and to do so in the shortest period of time, i.e., at a high speed, and to prepare the purest possible blood product that is uniform and contains only a few residual cells.

The device should also be as compact and as small as possible and should be simple and inexpensive to manufacture.

At the same time, the disadvantages of rotary drives that are known from the state of the art such as the high running noise, high cost of maintenance, wear and the generation of heat of friction should be avoided.

Another object of the invention is contamination-free, i.e., sterile, use.

This object is achieved according to the invention with the features defined in claim 1. The device has a magnetic drive device for separating blood into its components and has a container, which rotated about its own axis by the drive device, wherein the container has at least one open end and has at least one inlet in this open end and is suspended in a magnetically floating manner.

Advantageous embodiments of the invention are derived from the dependent claims.

This object is additionally achieved by the method described in claim 9 for separating blood into its components. This method may be used for continuous as well as discontinuous hemapheresis.

Advantageous embodiments of the invention are also derived here from the dependent claims.

Because of the magnetic drive device and the suspended mount, i.e., non-contact, there is no friction during operation of the cutting device. The rate at which the container is rotated can thus be increased and the container itself may be designed to be small and compact, so that it can also be embodied as a disposable article, for example.

In addition, all the disadvantages associated with a non-floating mount such as the high running noise, the heat of friction generated, the rapid wear and thus the associated high cost of maintenance are eliminated.

Claim 13 relates to a medical technical treatment unit having a device according to claim 1 which is designed as a disposable unit.

The device according to the invention may be part of a medical treatment device as defined in claim 14.

The use of the device according to the invention for separation of blood into its components relates to claim 15.

Figure 2:
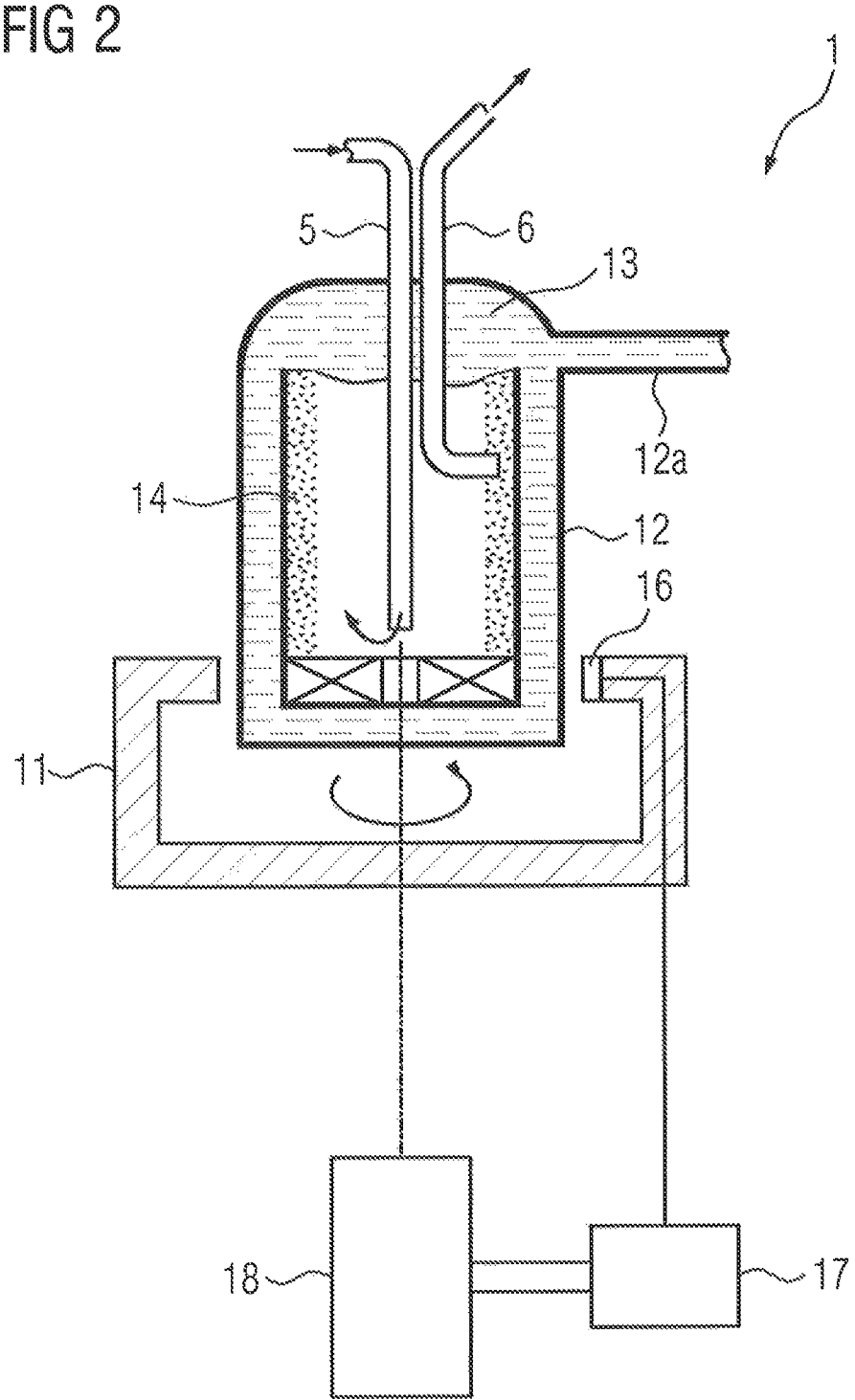

The invention is explained in greater detail below with reference to the drawings, in which:

FIG. 1: shows a simplified schematic diagram of the device according to the invention for separation of blood;

FIG. 2: shows a simplified schematic diagram of the device according to the invention for separation of blood with a housing surrounding the container;

FIGS. 3*a*-*d*: show various embodiments of the device according to the invention in a simplified schematic diagram.

FIG. 1 shows an device according to the invention for separation of blood in a simplified schematic diagram.

The device for separation of blood 1 has a container 2 and at least one bearing and drive device 11. The bearing and drive device 11 serves as a bearing for the container 2 and, at the same time, as a magnetic drive which is capable of inducing rotation of container 2 about its own axis.

The container 2 may be positioned vertically or horizontally or even obliquely, i.e., in stages between these two orientations.

With very tall containers, a counter-bearing may be mounted on the other end of the container 2 with respect to the bearing and drive device 11 to stabilize the container to prevent it from tilting.

The counter-bearing may be designed purely mechanically as a guide aid.

A magnetic embodiment of the counter-bearing in approximation to the bearing and drive device 11 is also conceivable, so that here again, a magnetically levitated and thus non-contact mount and, if necessary, an additional drive may also be provided here.

The container 2 has at least one inlet 5, which is situated on the at least one open end 3 of the container 2.

The open end 3 of the container 2 may be opened completely over the entire diameter of the container 2 or even to a lesser extent. The protrusion 15 formed with a less wide opening of the container 2 may serve as an overflow weir 10 for the outflowing blood plasma or blood serum 13, while the separated blood components 14 with a higher density are retained by it in the container 2.

At least one outlet 6 may also be provided on an open end 3 of the container 2.

The container 2 is made of a dimensionally stable material which is compatible with blood, for example, glass, metal or plastic. Of the plastics, polycarbonates have proven especially suitable. Use of thermoplastics or other dimensionally stable plastics that are compatible with blood is also conceivable.

The container 2 preferably has a cylindrical, shape, wherein the diameter 2a is min. 10 mm and max. 100 mm and the height to 2b is min. 20 mm and max. 900 mm, preferably 500 mm. The diameter 2a and height 2b can be varied and also influence one another mutually. Thus, if the diameter 2a is reduced, the height 2b must increase and vice versa, so that these two parameters are in a ratio to one another that is appropriate for the result of the separation, and the volume of the container 2 is not less than a minimum of 2 mL and does not exceed a maximum of 600 mL.

The container 2 is in contact with at least one magnet 9. The magnet 9 may be releasably or fixedly connected to the container 2 and/or may be a one-piece component with the same.

If the magnet 9 in one embodiment is releasably connected to the container 2, then it may be removed and reused before disposing of the container 2.

The magnet 9 may be situated in the interior of the container 2 or may also be on the outside of the container 2. If the magnet is mounted in the interior of the container, then it is a type of overflow weir 10 at the same time, so that the plasma is already separated at this location. This simplifies the separation process.

If the magnet is mounted on the outside of the container 2, it may advantageously be stored and reused when the container 2 is discarded.

The use of various types of magnets such as a shell magnet or a disk magnet or a ring magnet which completely or partially surrounds the container 2 is also conceivable.

Use of multiple small magnets which are grouped at a defined distance in or on the container 2 is also possible.

The parts of the device which come in contact with blood may be designed as reusable parts, but then they must be cleaned after each use. Therefore all blood-carrying parts are advantageously designed as disposable items. These can be discarded after use.

The device according to the invention has a bearing and drive device 11, which builds up a magnetic field and at the same serves as the bearing for the container 2 so that the container is held in a magnetically levitated position. The drive device may be operated electromagnetically. A drive by means of rotating permanent magnets, compressed air or fluid is also conceivable.

In the operating state, the container 2 rotates about its own axis, driven and held in suspension by the interaction between the magnetic field created electromagnetically by the bearing and drive device 11 and the magnet 9, which is either connected to the container 2 or integrated into it.

The rotational speed during operation is between 1000 and 50,000 revolutions per minute.

The centrifugal force occurring due to the rotation leads to the separation of the blood which is introduced into the container 2 through the inlet 5 at the first open end 3' or at the second open end 3" and is distributed on the inside of the wall of the rotating container 2. The blood components 14 that are separated are distributed according their density at different radial distances from the wall of the container 2, while the blood plasma and/or serum 13 is collected centrally in a container 2. The blood components and the blood plasma and/or serum 13 are forced in the direction of the open end of the container 2 by the blood being continuously resupplied.

A plasma flow of 1 mL/min to 300 mL/min is achieved, depending on the rotational speed.

A bearing and drive device 11 of the type described here is used, for example, by the company Levitronix for the drive for centrifugal pumps which are used to pump a fluid.

With the magnetically levitated mount, the position of the container 2 can be corrected by means of a control device 18, which controls the magnets to ensure a secure and accurately positioned mounting of the container 2 in the bearing and drive device for the duration of operation.

The functioning with respect to magnetic bearing and drive is described in detail in the documents EP 0 900 572 and EP 0 819 330, in particular, the contents of which are familiar to those skilled in the art and are herewith incorporated into the present description.

Due to the magnetic interaction and/or the resulting reluctance forces the container is stabilized to a certain extent even to prevent tipping.

In a particularly preferred embodiment, at least one sensor 16 is integrated into the device; by means of the sensor together with an evaluation unit 17, it is possible to obtain information about the position of the container.

An embodiment of the blood-separating device according to the invention in the form oil a disposable cassette as a medical technical treatment unit is also conceivable.

The device according to the invention may be part of a medical treatment device.

The device according to the invention may be used for separation of blood.

FIG. 2 shows a simplified schematic diagram of the device according to the invention for separation of blood with a housing 12 which surrounds the container 2.

The container 2 may advantageously be surrounded by a housing 12. The housing 12 spatially separates blood and blood components 14 from the bearing and drive device 11. If unforeseen contaminants from the surroundings around the container 2 occur in introducing or removing blood components 14 or even if the container 2 itself has a defect, the user is protected from contact with possible infectious material. All cost-intensive parts such as the bearing and drive device 11 of the container 2 are not contaminated and may continue being used.

Conversely, the blood to be treated and its components are protected from contaminants, thereby ensuring sterility.

If the device is operated in the manner of an overflow centrifuge, the housing 12 may also serve as a collecting vessel for overflow of blood plasma and/or serum 13. It is conceivable to flood the space around the container 2 completely with blood plasma or serum 13.

If the housing 12 has an outlet 12a, then blood plasma or serum 13 can be removed. The blood components 14 remaining in the container 2 are removed separately.

Figure 3A:
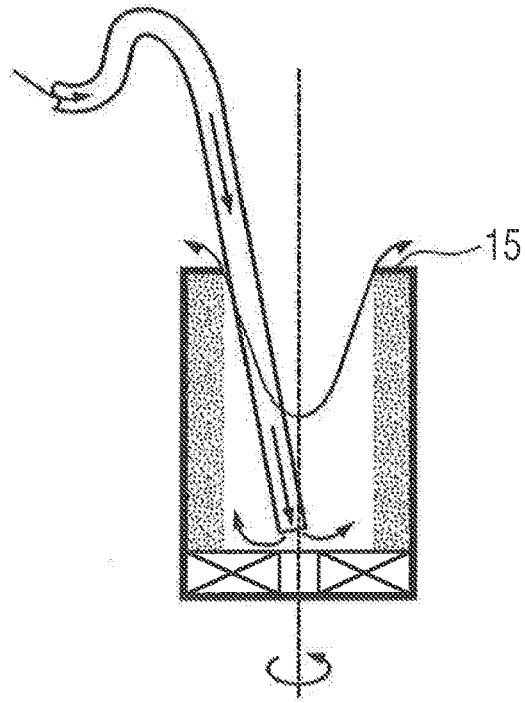

FIG. 3a shows an embodiment of the device 1 according to the invention in a simplified schematic diagram in which the magnets 9 are located on the closed end 4 of the container 2.

Figure 3B:
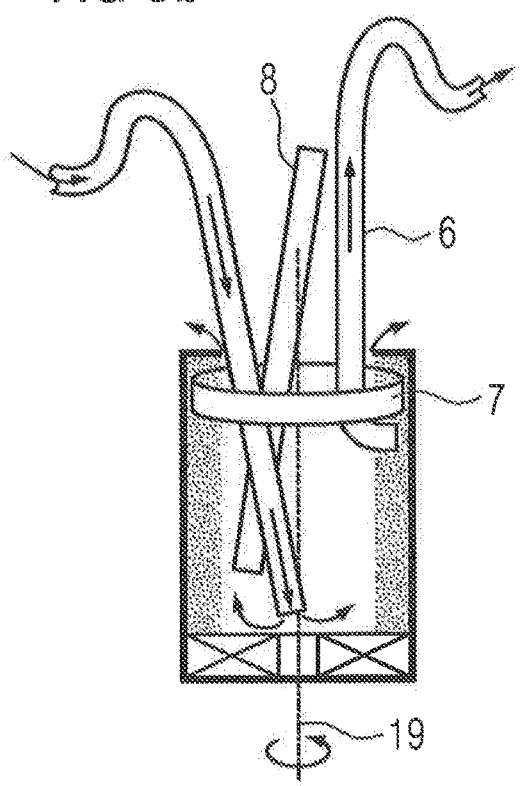

FIG. 3b shows an embodiment of the device 1 according to the invention in a simplified schematic diagram in which the magnets 9 are on the closed end 4 of the container 2 and a module 7 having means for removing the blood components 8 from the at least one open end 3 of the container 2 is accommodated.

It is also conceivable that the module 7 is designed so that individual blood components 14 may themselves be removed with it, for example, in that the blood components 14 are released from the wall of the container and conveyed outward, while the edge of the module 7 is in contact with the inside edge of the container 2.

Inlet 5 and/or outlet 6 may also be integrated into the module 7.

Figure 3C:
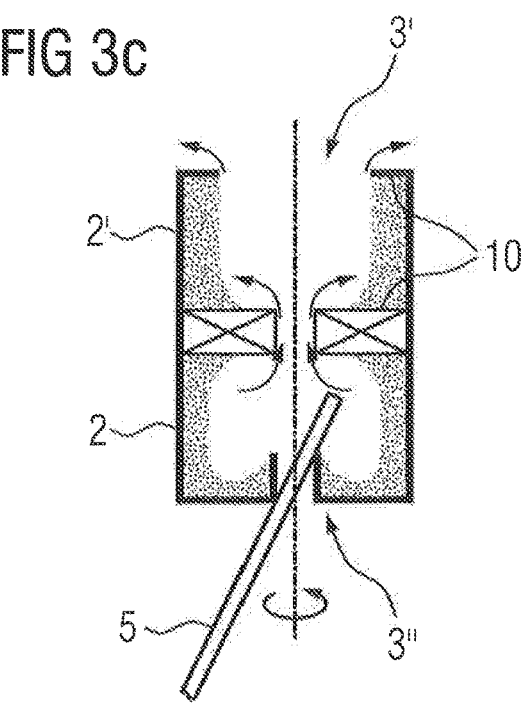

FIG. 3c shows an embodiment of the device 1 according to the invention in a simplified schematic diagram in which the magnets 7 are mounted at half height within the container 2. In this embodiment, the container 2 has a first open end 3' and a second open end 3".

The blood is introduced through the lower end 3" while the blood components having a higher density collect beneath the magnets 9 in the lower section 2" of the container 2 during rotation while the blood plasma or blood serum 13 having a lower density overcomes the magnets 19 and moves into the upper section 2' of the container 2. The magnets 9 then serve as an overflow weir 10.

Figure 3D:
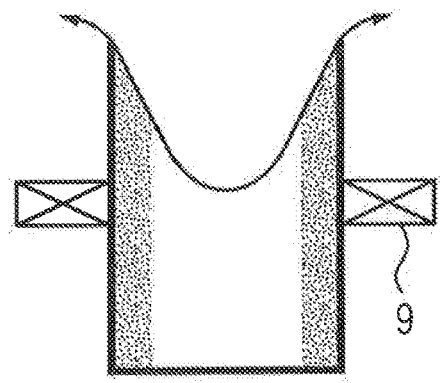

FIG. 3d shows an embodiment of the device 1 according to the invention in a simplified schematic diagram, in which the magnets 9 are mounted on the exterior of the container 2.

In addition to the embodiments describe above, additional embodiments with variations of the aforementioned features are of course also conceivable.

LIST OF REFERENCE NUMERALS

Device for separation of blood 1
Container 2
Upper section of the container 2'
Lower section of the container 2"
Diameter of the container 2a
Height of the container 2b
Open end 3
First open end 3'
Second open end 3"
Closed end 4
Inlet 5
Outlet 6
Module 7
Means for removing the blood components 8
Magnet 9
Overflow weir 10
Bearing and drive device 11
Housing 12
Outlet of the housing 12a
Blood plasma/serum 13
Separated blood components 14
Protrusion 15
Sensor 16
Evaluation unit 17
Control device 18
Axis of rotation 19

The invention claimed is:

1. A device for separating blood into its components, comprising
   a magnetic bearing and drive device,
   a container having a cylindrical shape suspended during operation in the bearing and drive device in a magnetically floating manner, having an axis, about which axis the container is rotated by the bearing and drive device during operation, and having at least one open end,
   at least one tube-shaped inlet and at least one outlet provided, independently, in the at least one open end of the container,
   at least one magnet connected to, or integrated into, the container, and
   a control device configured to control the at least one magnet and the magnetic bearing and drive device for securing and accurately positioning the container in the bearing and drive device during operation.

2. The device according to claim 1, further comprising
   a module accommodated by the at least one open end of the container, which module integrates therein the at least one inlet, the at least one outlet, or the at least one inlet and the at least one outlet and has means for removing the blood components that have been separated.

3. The device according to claim 1, characterized in that the container is made of a dimensionally stable material that is compatible with blood.

4. The device according to claim 1, characterized in that the container has a diameter of at least 10 mm and max. 100 mm and a height of at least 20 mm and max. 900 mm.

5. The device according to claim 1, characterized in that the at least one magnet is connected to the container, either releasably or fixedly, and is situated outside the container or inside the container.

6. The device according to claim 1, characterized in that the container is surrounded by a housing.

7. The device according to claim 1, characterized in that all blood-carrying parts are designed as disposable articles.

8. A method for separating blood into its components, comprising a container according to claim 1, wherein the method comprises the following steps:
   introducing blood into the container
   driving the container to rotate about its own axis
   removing the blood components
characterized in that
the container is suspended in a magnetically floating manner during the separation process.

9. The method according to claim 8, characterized in that the position of the container is detected by at least one sensor and is stabilized or corrected by an evaluation unit with the help of a control device.

10. The method according to claim 8, characterized in that the rotational speed in rotation is between 1000 and 50,000 revolutions per minute.

11. The method according to claim 10, characterized in that a plasma flow rate of 1 mL/min to 300 mL/min is achieved.

12. A medical technical treatment unit having the device according to claim 1, which is designed as a disposable unit.

13. The device according to claim 1 for separation of blood into its components as part of a medical technical treatment device.

14. The device according to claim 1, characterized in that the container is made of dimensionally stable plastic compatible with blood.

15. The device according to claim 1, characterized in that the container is made of polycarbonate.

16. The device according to claim 1, characterized in that the container has a diameter of at least 10 mm and max. 100 mm and a height of at least 20 mm and max. 500 mm.

17. The device according to claim 1, characterized in that the container has a diameter of at least 10 mm and max. 100 mm and a height of at least 20 mm and max. 500 mm, wherein the container has a minimum volume of 2 mL and a maximum volume of 600 mL.

18. The device according to claim 1, characterized in that the container has a diameter of at least 10 mm and max. 100 mm and a height of at least 20 mm and max. 900 mm, wherein the container has a minimum volume of 2 mL and a maximum volume of 600 mL.

19. The device according to claim 1, characterized in that the at least one magnet is integrated into the container forming a single piece.

* * * * *